US010989631B2

(12) United States Patent
Seidel et al.

(10) Patent No.: US 10,989,631 B2
(45) Date of Patent: Apr. 27, 2021

(54) SAMPLING DEVICE FOR TAKING BEVERAGE SAMPLES FROM A BEVERAGE LINE CONTAINING A CARBONATED BEVERAGE UNDER PRESSURE

(71) Applicant: QFood GmbH, Gundelfingen (DE)

(72) Inventors: Robert Seidel, Freiburg im Breisgau (DE); Holger Klapproth, Freiburg im Breisgau (DE); Martina Auerswald, Bad Homburg (DE)

(73) Assignee: QFood GmbH, Gundelfingen (DE)

( * ) Notice: Subject to any disclaimer, the term of this patent is extended or adjusted under 35 U.S.C. 154(b) by 143 days.

(21) Appl. No.: 16/308,174

(22) PCT Filed: Jun. 8, 2017

(86) PCT No.: PCT/EP2017/064011
§ 371 (c)(1),
(2) Date: Jan. 9, 2019

(87) PCT Pub. No.: WO2017/211980
PCT Pub. Date: Dec. 14, 2017

(65) Prior Publication Data
US 2019/0301981 A1    Oct. 3, 2019

(30) Foreign Application Priority Data

Jun. 10, 2016   (DE) ..................... 10 2016 007 094.3

(51) Int. Cl.
*G01N 1/14*    (2006.01)
*G01N 1/20*    (2006.01)
(Continued)

(52) U.S. Cl.
CPC ................. *G01N 1/14* (2013.01); *G01N 1/20* (2013.01); *G01N 1/2035* (2013.01); *G01N 1/34* (2013.01);
(Continued)

(58) Field of Classification Search
CPC ........ G01N 33/14; G01N 33/143; G01N 1/14; G01N 1/18; G01N 1/2042;
(Continued)

(56) References Cited

U.S. PATENT DOCUMENTS 3,673,853 A * 7/1972 Griswold ................. G01N 7/14
73/19.1
3,789,670 A * 2/1974 Rosenwald .......... G01N 1/2042
73/864.62
(Continued)

FOREIGN PATENT DOCUMENTS

DE         3920949 A1    1/1991
DE        10352924 A1    7/2005
(Continued)

*Primary Examiner* — Tran M. Tran
(74) *Attorney, Agent, or Firm* — The Webb Law Firm (57) ABSTRACT

A sampling device for taking samples from a gaseous beverage under pressure includes a connection for a beverage line, a pump having a pump chamber, a particle filter, a discharging opening for a beverage sample, an outlet for waste, a control device, and a line system connected to the pump chamber with adjustable valves. The sampling device is configured so a beverage sample with a volume smaller than the volume of the pump chamber is introduced from the connection into the pump chamber. The pump chamber is then separated from the connection and is expanded so gas exits from the beverage sample. The pump chamber is then connected to the outlet opening and compressed so gas which has passed out of the beverage sample is displaced. Then, the pump chamber is connected to the discharging opening via the particle filter and compressed so the beverage sample is displaced.

16 Claims, 6 Drawing Sheets

(51) Int. Cl.
*G01N 1/34* (2006.01)
*G01N 33/14* (2006.01)
*G01N 1/10* (2006.01)

(52) U.S. Cl.
CPC ..... *G01N 33/146* (2013.01); *G01N 2001/105* (2013.01); *G01N 2001/205* (2013.01); *G01N 2001/2057* (2013.01)

(58) Field of Classification Search
CPC .... G01N 2001/02064; G01N 2001/1418–149; G01N 2001/205; G01N 2001/2057; G01N 2001/247
See application file for complete search history.

(56) References Cited

U.S. PATENT DOCUMENTS

| | | | | |
|---|---|---|---|---|
| 3,942,356 A * | 3/1976 | Branscombe | G01N 33/14 | 73/19.06 |
| 4,013,413 A * | 3/1977 | Stewart | G01N 35/08 | 436/53 |
| 4,037,475 A * | 7/1977 | Topham | G01N 1/2035 | 73/863.01 |
| 4,204,962 A * | 5/1980 | Ford | B01D 37/00 | 210/316 |
| 4,257,259 A * | 3/1981 | Ford | B01D 37/00 | 73/61.56 |
| 4,307,620 A * | 12/1981 | Jiskoot | G01N 1/2035 | 73/863.61 |
| 4,343,231 A * | 8/1982 | Devreux | C12M 29/18 | 99/277.2 |
| 4,470,316 A * | 9/1984 | Jiskoot | G01N 1/2042 | 222/249 |
| 4,527,436 A * | 7/1985 | Jones | G01N 1/14 | 73/863.84 |
| 4,745,794 A * | 5/1988 | Steichen | G01N 7/14 | 73/19.03 |
| 4,763,514 A * | 8/1988 | Naito | G01N 33/2841 | 73/19.01 |
| 4,800,763 A * | 1/1989 | Hakkers | G01N 1/22 | 73/863 |
| 4,910,996 A * | 3/1990 | Pfisterer | G01N 30/32 | 422/89 |
| 4,932,272 A * | 6/1990 | Hogg | G01N 30/20 | 73/23.35 |
| 4,942,770 A * | 7/1990 | Seifert | C12M 33/00 | 73/864.34 |
| 4,955,992 A * | 9/1990 | Goodale | B01D 19/0031 | 96/197 |
| 4,987,083 A * | 1/1991 | Apple | B67D 1/0016 | 141/105 |
| 5,068,116 A * | 11/1991 | Gibney | B67D 1/0016 | 426/231 |
| 5,116,330 A * | 5/1992 | Spencer | G01N 1/2035 | 73/863.71 |
| 5,131,226 A * | 7/1992 | Hendry | B29C 45/1732 | 60/418 |
| 5,192,984 A * | 3/1993 | Beecher | G01N 1/44 | 250/576 |
| 5,220,513 A * | 6/1993 | Seiden | G01N 1/2226 | 702/24 |
| 5,275,786 A * | 1/1994 | Soleta | B01J 19/0053 | 422/68.1 |
| 5,279,647 A * | 1/1994 | Gatten | B01D 19/0031 | 96/193 |
| 5,361,643 A * | 11/1994 | Boyd | G01N 1/2035 | 73/863.71 |
| 5,433,120 A * | 7/1995 | Boyd | G01N 1/2035 | 73/863.71 |
| 5,717,131 A * | 2/1998 | Sunde | G01N 11/08 | 73/64.41 |
| 5,736,654 A * | 4/1998 | Dubois | G01N 1/2042 | 73/863.84 |
| 6,112,604 A * | 9/2000 | Peterson | G01N 1/18 | 73/863 |
| 7,169,599 B2 * | 1/2007 | Barringer, Jr. | B01D 61/142 | 435/286.5 |
| 7,690,245 B2 * | 4/2010 | Jung | G01N 1/2042 | 73/53.01 |
| 7,951,597 B2 * | 5/2011 | Usowicz | G01N 1/14 | 422/501 |
| 7,955,843 B2 * | 6/2011 | Barringer, Jr. | B01D 61/142 | 137/240 |
| 8,092,744 B1 * | 1/2012 | Meece | G01N 30/12 | 422/68.1 |
| 8,857,240 B2 * | 10/2014 | Tastard | B01D 19/0036 | 73/19.01 |
| 9,285,347 B2 * | 3/2016 | Satake | G01N 30/04 | |
| 9,389,151 B2 * | 7/2016 | Newbold | G01N 1/10 | |
| 9,435,773 B2 * | 9/2016 | Glatz | G01N 30/20 | |
| 9,442,047 B2 * | 9/2016 | Biksacky | G01N 1/2035 | |
| 9,499,782 B2 * | 11/2016 | Newbold | C12M 33/04 | |
| 9,846,109 B2 * | 12/2017 | Hall | B08B 5/02 | |
| 10,107,728 B2 * | 10/2018 | Mostowfi | B01D 1/30 | |
| 10,421,939 B2 * | 9/2019 | Ray | C12M 29/18 | |
| 10,481,049 B2 * | 11/2019 | Pellerin | G01N 1/20 | |
| 10,674,749 B2 * | 6/2020 | Lucas | A23L 2/76 | |
| 2004/0238745 A1 * | 12/2004 | Pedersen | G01N 33/14 | 250/343 |
| 2015/0338323 A1 * | 11/2015 | Heub | G01N 1/405 | 73/863.23 |
| 2016/0258846 A1 * | 9/2016 | Kunnecke | B65B 3/003 | |
| 2017/0130180 A1 * | 5/2017 | Mitter | C12C 7/161 | |

FOREIGN PATENT DOCUMENTS

| | | |
|---|---|---|
| DE | 202014106092 U1 | 4/2016 |
| EP | 0367899 A1 | 5/1990 |
| EP | 1035407 A2 | 9/2000 |
| WO | 2004034035 A1 | 4/2004 |

* cited by examiner

SAMPLING DEVICE FOR TAKING BEVERAGE SAMPLES FROM A BEVERAGE LINE CONTAINING A CARBONATED BEVERAGE UNDER PRESSURE

CROSS-REFERENCE TO RELATED APPLICATIONS

This application is the United States national phase of International Application No. PCT/EP2017/064011 filed Jun. 8, 2017, and claims priority to German Patent Application No. 10 2016 007 094.3 filed Jun. 10, 2016, the disclosures of which are hereby incorporated in their entirety by reference.

BACKGROUND OF THE INVENTION

Field of the Invention

The invention relates to a sampling device for taking beverage samples from a beverage line containing a carbonated beverage under pressure, wherein the sampling device has
- a connector for the beverage line,
- a pump having a drive, which pump has a pump chamber that is delimited by walls, which can be moved toward and away from one another, by means of the drive, for expanding and compressing the pump chamber,
- a discharging opening for the beverage sample,
- a line system having adjustable valves, which system is connected with the connector for the beverage line, the pump chamber, and the discharging opening, and
- a control device.

Description of Related Art

Such a sampling device is known from DE 103 52 924 A 1. It has a connector for a beverage line of a beverage production facility. A carbonated beverage, such as beer, for example, flows through the beverage line under pressure. The connector for the beverage line is connected with a discharging opening for the beverage sample by way of a feed line, which is connected at an inlet opening of a throughflow measurement cell of an infrared spectrometer. A coarse-particle filter is disposed in the feed line between the connector for the beverage line and the discharging opening, which filter has a pore size between 1 μm and 0.1 mm. The outlet opening of the throughflow measurement cell is connected with an outlet for the beverage sample by way of a fluid line in which a conductivity sensor, a pH sensor, a turbidity sensor, a needle valve, a shut-off valve, and an intake pump are disposed. A return line branches off from the fluid line between the turbidity sensor and the needle valve. The beverage sample can be returned into the production process by way of the return line, if necessary. However, this does not meet the safety requirements according to the guidelines of the European Hygienic Engineering & Design Group (EHEDG) that must be adhered to in the production of foods, according to which no liquids from the sampling device are allowed to enter back into the beverage line of the food packaging device.

The needle valve, which is disposed behind the throughflow measurement cell in the flow direction, and the shut-off valve, which is disposed behind the needle valve in the flow direction, serve to maintain a pressure of 2 to 5 atmospheres in the throughflow measurement cell during analysis of carbonated beverages. However, pressure-sensitive analysis devices such as the QFOOD QUANTOS®, for example, are not suitable for such high pressures. It is true that it is also possible to work under normal pressure conditions using the sampling device if the needle valve and/or the shut-off valve are open. However, this has the disadvantage that gas bubbles can then form in the beverage sample, which bubbles can cause functional problems of the analysis device, in particular if the beverage sample is being transported through very thin fluid channels and/or a throughflow measurement cell in which the beverage sample forms a thin layer between walls that are disposed parallel to one another at a slight distance.

The task therefore exists of creating a sampling device having a robust construction, by means of which a beverage sample can be taken, in simple manner, from a beverage line containing a carbonated beverage under pressure, and passed to an analysis device, in particular an infrared spectrometer, under normal pressure at a discharging opening. In this regard, gas bubbles in the beverage sample are supposed to be prevented at the discharging opening.

SUMMARY OF THE INVENTION

According to the invention, this task is accomplished with a sampling device of the type stated initially, that an outlet opening for waste is connected with the line system, and that the line system is configured in such a manner I) that in a first valve configuration, the pump chamber is connected with the connector for the beverage line, and separated from the outlet opening and from the discharging opening, II) that in a second valve configuration, the pump chamber is separated from the connector for the beverage line, from the outlet opening, and from the discharging opening, III) that in a third valve configuration, the pump chamber is connected with the outlet opening and separated from the connector for the beverage line and from the discharging opening, IV) that in a fourth valve configuration, the pump chamber is connected with the discharging opening and separated from the connector for the beverage line and from the outlet opening, and that the control device stands in a control connection with the pump and the valves, in such a manner i) that in the first valve configuration, a beverage sample, the volume of which is smaller than the maximal volume of the pump chamber, can be introduced from the connector for the beverage line into the pump chamber, ii) that afterward, the second valve configuration is set, and the pump chamber is expanded in such a manner that a partial vacuum occurs in the pump chamber, so as to remove gas from the beverage sample, iii) that afterward, the third valve configuration is set, and the pump chamber is compressed in such a manner that a first partial volume situated in an upper part of the pump chamber is displaced toward the outlet opening, and a second partial volume situated in a lower part of the pump chamber remains in the pump chamber, and iv) that afterward, the fourth valve configuration is set, and the pump chamber is compressed further to displace the beverage sample situated in it, toward the discharging opening.

In advantageous manner, the pump chamber performs a dual function in this regard, in that it serves for removing gas from the beverage sample, on the one hand, and, on the other hand, is used for transport of the degassed beverage sample from the pump chamber to the discharging opening for the beverage sample. This allows a simple and robust structure of the sampling device. Since the beverage sample is discharged at the discharging opening essentially under atmospheric pressure, the sampling device can also be combined with analysis devices in which the analyte is not allowed to have any excess pressure or allowed to have only a very slight excess pressure. Since the beverage sample is degassed before it reaches the discharging opening, and since the gas that exits from the beverage sample and is situated in the upper part of the pump chamber is conducted away by way of the outlet opening, gas bubbles in the beverage sample, which could lead to functional problems of the analysis device, are prevented at the discharging opening. The pump is preferably configured as a syringe pump or as a piston pump. This measure also allows a simple and robust structure of the sampling device.

In a preferred embodiment of the invention, the control device is configured in such a manner that steps ii) and iii) of claim 1 are repeated at least once before step iv) of claim 1 is carried out. As a result, the gas content of the beverage sample can be further reduced.

In a further development of the invention, the sampling device has a particle filter having an inlet and an outlet for filtering the beverage sample, wherein the line system is connected with the inlet of the particle filter, the outlet of the particle filter, and a feed line for a backflushing medium, that in the fourth valve configuration, the pump chamber is connected with the discharging opening by way of the particle filter, that in the first, second, third, and fourth valve configuration, the pump chamber is separated from the feed line for the backflushing medium, that in a fifth valve configuration, the feed line for the backflushing medium is connected with the outlet opening by way of the particle filter, and that the control device stands in a control connection with the valves, in such a manner that after step iv) of claim 1, the fifth valve configuration is set for backflushing of the particle filter. The particle filter prevents any particles that might be contained in the beverage sample from entering the discharging opening for the sample and thereby into an analysis device connected with the opening and provided for analyzing the beverage sample. Since the particle filter is automatically backflushed after use, particles that have been held back out of the beverage sample by the particle filter can be easily removed from the particle filter again and conducted away out of the sampling device by way of the outlet opening. This allows low-maintenance and problem-free operation of the sampling device.

Preferably, in the second and/or third valve configuration, the pump chamber is separated from the inlet of the particle filter. In this way, gas bubbles are prevented from entering into the particle filter from the pump chamber. In the first valve configuration, as well, the pump chamber can be separated from the inlet of the particle filter.

In an advantageous embodiment of the invention, the particle filter has a pre-filter and a micro-filter set in series with it, wherein the inlet of the particle filter is disposed on the pre-filter, and the outlet of the particle filter is disposed on the micro-filter. Particles up to a size of preferably 0.4 μm can be filtered out of the beverage sample by means of the micro-filter. The pre-filter that precedes the micro-filter filters larger particles out of the beverage sample. In this way, the useful lifetime of the micro-filter is increased.

In a preferred embodiment of the invention, the connector for the beverage line is connected with the pump chamber by way of a first line, wherein a first shutoff valve is disposed in the first line, wherein the pump chamber is connected with the first line by way of a second line that opens into the pump chamber, or at a first branching location disposed between this chamber and the first shutoff valve, and is connected with a first fluid connector of a first three-way valve, and wherein a second fluid connector of the first three-way valve is connected with the outlet opening, and a third fluid connector of the first three-way valve is connected with the inlet of the particle filter. In this regard, the three-way valve allows a simple structure of the line system.

In another practical embodiment of the invention, the connector for the beverage line is connected with the pump chamber by way of a first line, wherein a first shutoff valve is disposed in the first line, wherein the pump chamber is connected with the first line by way of a second line that opens into the pump chamber, or at a first branching location disposed between the chamber and the first shutoff valve, and is connected with the inlet of the particle filter, wherein a second shutoff valve is disposed in the second line, and wherein a connection location is provided at the pump chamber and/or at the first line, between the pump chamber and the first shutoff valve and/or on the second line, between the pump chamber and the second shutoff valve, which line is connected with the outlet opening for waste by way of a third shutoff valve. Instead of the first three-way valve, two shutoff valves can therefore also be provided.

The sampling device according to the invention is preferably designed to be compatible with the guidelines of the European Hygienic Engineering & Design Group (EHEDG). In particular, the sampling device can be configured in such a manner that no fluids that are disposed behind the first shutoff valve in the sampling device can flow back into the beverage line. This can be achieved in that the first shutoff valve is always closed during compression of the pump chamber.

In a further development of the invention, at least one sensor connected with the control device for detection of the beverage is disposed in the line system between the connector for the beverage line and the inlet of the particle filter and/or between the pump chamber and the inlet of the particle filter, wherein the control device is configured in such a manner that the inlet of the particle filter is shut off by means of the first three-way valve or of the second shutoff valve, if the sensor does not detect the beverage. The inlet of the particle filter is then blocked, if the sensor comes into contact with a gas and/or with a cleaning fluid, disinfection fluid and/or flushing fluid, which is passed through the beverage line within the scope of a Cleaning in Place cleaning method (CIP). Using the CIP cleaning method that is usual in the foods industry, a production facility for beverages can be cleaned on the surfaces that come into contact with the beverage, without significant disassembly. The sampling device according to the invention is therefore also suitable for use in production facilities that are cleaned and/or disinfected using the CIP cleaning method.

It is practical if the sensor has a conductivity sensor and/or a pH sensor. This allows a cost-advantageous embodiment of the sensor.

In an advantageous embodiment of the invention, the outlet of the particle filter is connected with a first fluid connector of a second three-way valve, wherein a second fluid connector of the second three-way valve is connected with the discharging opening for the beverage sample, and a third fluid connector of the second three-way valve is connected with the feed line for the backflushing medium. In this regard, the second three-way valve allows a simple structure of the line system.

In another embodiment of the invention, it is provided that the outlet of the particle filter is connected with the discharging opening for the beverage sample by way of a third line in which a fourth shutoff valve is disposed, and that a second branching location is disposed between the outlet of the particle filter and the fourth shutoff valve, at which the third line is connected with the feed line for the backflushing medium by way of a fifth shutoff valve. Instead of the second three-way valve, two shutoff valves can also be provided.

In a preferred embodiment of the invention, it is provided that the connector for the beverage line is connected with the pump chamber by way of a first line, that in the first line, the first shutoff valve and a sixth shutoff valve are switched in series, that the pump chamber or a first branching location provided in the first line, between the sixth shutoff valve and the pump chamber, is connected with the inlet of the particle filter by way of the second line, and that a third branching location is disposed between the first shutoff valve and the sixth shutoff valve, with which the first line is connected with the outlet opening or a further outlet opening for waste by way of a fourth line, in which a seventh shutoff valve is disposed.

In this regard, the first, sixth, and seventh shutoff valves can be configured, when a cleaning fluid, disinfection fluid and/or flushing fluid is passed through the beverage line by means of the control device, in such a manner that the first and seventh shutoff valves are open, and the sixth shutoff is closed. The cleaning fluid, disinfection fluid and/or flushing fluid can then flow from the connector for the beverage line, by way of the first shutoff valve and the first line, to the third branching location, and from there, by way of the fourth line and the seventh shutoff valve, to the outlet opening. Since the sixth shutoff valve is closed in this configuration, the cleaning fluid, disinfection fluid and/or flushing fluid cannot enter into the pump chamber or the particle filter. In a further configuration, which serves for filling the pump chamber with the beverage sample, the first and sixth shutoff valves are open, and the seventh shutoff valve is closed. If needed, the first, sixth, and seventh shutoff valves can also be set in such a manner, by way of the control device, that the seventh shutoff valve is open, and the first and sixth shutoff valves are closed. As a result, no fluid can flow back out of the pump chamber into the beverage line, if the first and/or sixth shutoff valve were to develop a leak.

BRIEF DESCRIPTION OF THE DRAWINGS

In the following, exemplary embodiments of the invention are explained in greater detail using the drawing. This shows.

DESCRIPTION OF THE INVENTION

Figure 1:
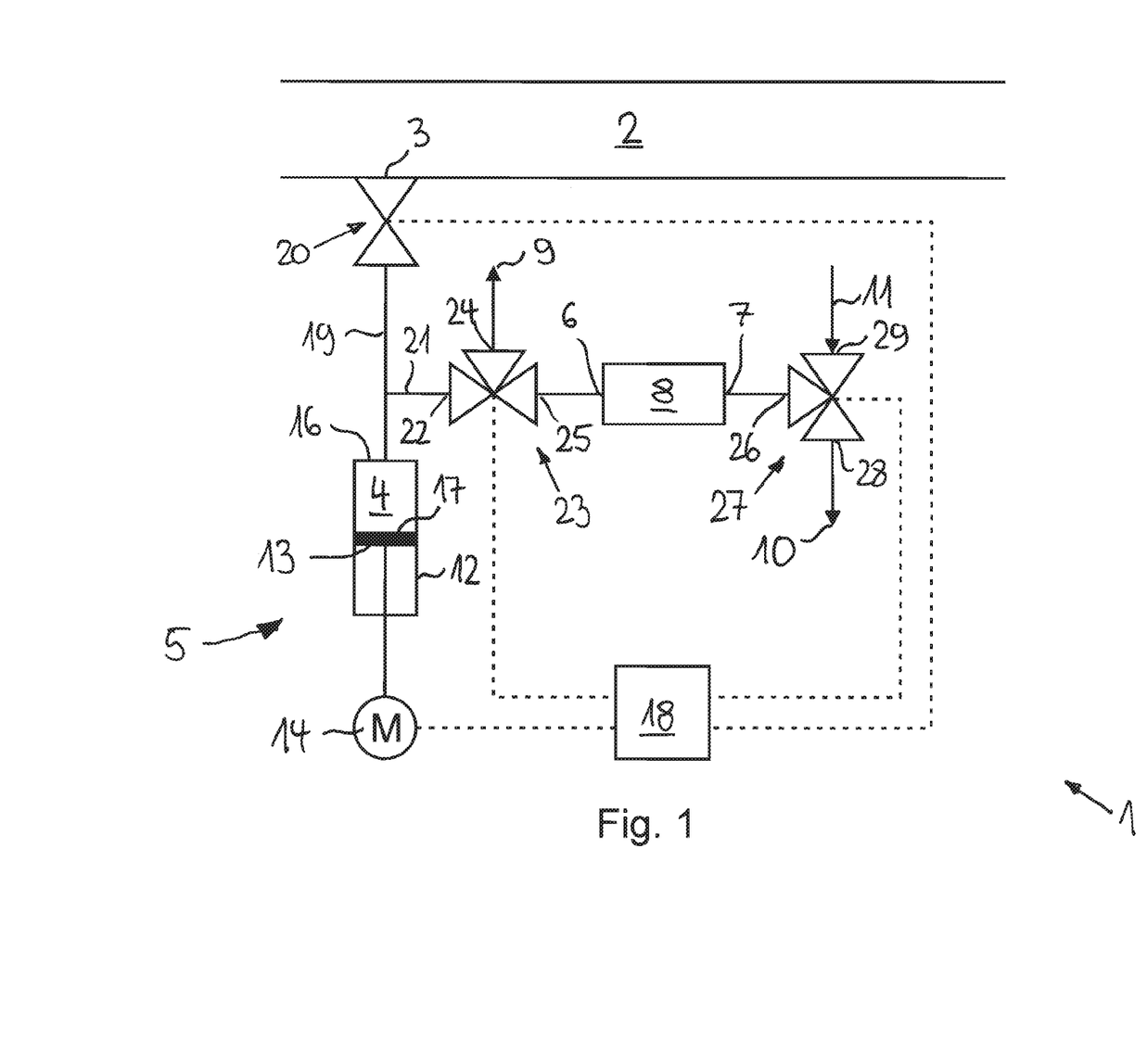
FIG. 1 a schematic representation of a first exemplary embodiment of the sampling device, FIG. 2 a schematic representation of a second exemplary embodiment of the sampling device, FIG. 3 a schematic representation of a third exemplary embodiment of the sampling device, FIG. 4 a schematic representation of a fourth exemplary embodiment of the sampling device, FIG. 5 a schematic representation of a fifth exemplary embodiment of the sampling device, and FIG. 6 a schematic representation of a sixth exemplary embodiment of the sampling device.

A sampling device referred to in FIG. 1 as 1, as a whole, serves for taking beverage samples from a beverage line 2 in a beverage production facility. A carbonated beverage, for example beer or a carbonated soda, under pressure, is contained in the beverage line 2.

The sampling device 1 has a connector 3, shown only schematically in FIG. 1, which is firmly connected with the beverage line 2. The connector 3 is connected, by way of a line system that has valves that can be adjusted by means of actuators, which are not shown in any detail in the drawing, with a pump chamber 4 of a pump 5, a particle filter 8 that has an inlet 6 and an outlet 7, for filtering the beverage sample, an outlet opening 9 for waste, a discharging opening 10 for the beverage sample, and a feed line 11 for a backflushing medium. An analysis device not shown in any detail in the drawing, such as the QFOOD QUANTOS®, for example, can be connected at the discharging opening 10, which device serves for examining the beverage sample.

The pump 5 is configured as a syringe pump, which has a piston 13 that can be axially displaced in a cylinder 12, and can be adjusted by means of a drive 14 that is shown only schematically in the drawing. The cylinder 12 and the piston 13 delimit a pump chamber 4, which is delimited at its upper end by an upper wall 16, at its lower end by a lower wall 17 formed by the piston 13, and laterally by the inner wall of the cylinder 12, which wall encloses the pump chamber 4. For expansion and compression of the pump chamber 4, the piston 13 can be moved toward the upper wall 16 and away from it by means of the drive 14.

Using the valves, the line system can be configured as follows:

I) In a first valve configuration, the pump chamber 4 is connected with the connector 3 for the beverage line 2, and separated from the outlet opening 9 for waste, the discharging opening 10 for the beverage sample, and the feed line 11 for the backflushing medium.

II) In a second valve configuration, the pump chamber 4 is separated from the connector 3 for the beverage line, the outlet opening 9 for waste, the discharging opening 10 for the beverage sample, and the feed line 11 for the backflushing medium.

III) In a third valve configuration, the pump chamber 4 is connected with the outlet opening 9 for waste, and separated from the connector 3 for the beverage line 2, the discharging opening 10 for the beverage sample, and the feed line 11 for the backflushing medium.

IV) In a fourth valve configuration, the pump chamber 4 is connected with an inlet 6 of the particle filter 8, and the outlet 7 of the particle filter 8 is connected with the discharging opening 10 for the beverage sample. Furthermore, the pump chamber 4 is separated from the connector 3 for the beverage line 2, the outlet opening 9 for waste, and the feed line 11 for the backflushing medium.

V) In a fifth valve configuration, the feed line 11 for the backflushing medium is connected with the outlet opening 9 for waste by way of the particle filter 8, and separated from the connector 3 for the beverage line 2, the pump chamber 4, and the discharging opening 10.

In the first exemplary embodiment shown in FIG. 1, the connector 3 for the beverage line 2 is connected with the upper end of the pump chamber 4 by way of a first line 19. It can be clearly seen that the first line 19 opens into the pump chamber 4 at the upper wall 16.

In the first line, directly adjacent to the connector 3, a first shutoff valve 20 is disposed, by means of which the first line 19 can be closed off toward the beverage line 2. The first line 19 has a first branching location, at which the first line 19 is connected with a first fluid connector 22 of a first three-way valve 23 by way of a second line 21, between the first shutoff valve 20 and the pump chamber 4. A second fluid connector 24 of the first three-way valve 23 is connected with the outlet opening 9 for waste, and a third fluid connector 25 of the first three-way valve 23 is connected with the inlet 6 of the particle filter 8.

The outlet 7 of the particle filter 8 is connected with a first fluid connector 26 of a second three-way valve 27, a second fluid connector 28 of the second three-way valve 27 is connected with the discharging opening 10 for the beverage sample, and a third connector 29 of the second three-way valve 27 is connected with the feed line 11 for the backflushing medium.

As can be seen in FIG. 1, the sampling device 1 furthermore has a control device 18. This device stands in a control connection with the first shutoff valve 20, the three-way valves 23, 27, and the drive 14 of the pump 5, in such a manner that the following steps are performed:
  i) In the first valve configuration, a beverage sample, the volume of which is less than the maximal volume of the pump chambers 4, is introduced from the connector 3 for the beverage line 2 into the pump chamber 4. This can be achieved, for example, in that the first valve configuration is set for a predetermined period of time adapted to the volume of the beverage sample and the volume stream in the first line 19.
  ii) Afterward, a second valve configuration is set, and the pump chamber 4 is expanded in such a manner that gas exits from the beverage sample. In this regard, the period during which the pump chamber 4 is expanded is selected in such a manner that gas can exit from the beverage sample in a noteworthy amount, and enter into the part of the pump chamber 4 that is situated above the beverage sample.
  iii) Afterward, the third valve configuration is set, and the pump chamber 4 is compressed in such a manner that gas that has exited from the beverage sample and is situated in the upper part of the pump chamber 4 is displaced toward the outlet opening 9 for waste, and the beverage sample situated in the lower part of the pump chamber 4 remains essentially within the pump chamber 4.
  iv) Steps ii) and iii) of claim 1 are repeated at least once.
  v) Afterward, the fourth valve configuration is set, and the pump chamber 4 is further compressed in such a manner that the beverage sample situated in it is displaced toward the discharging opening 10. In this regard, the beverage sample flows through the particle filter 8.
  vi) Afterward, the fifth valve configuration is set for backflushing of the particle filter 8. In this regard, clean water flows out of the feed line 11, counter to the flow direction of the beverage sample, through the particle filter 8, to the outlet opening 9, where it is passed into the sewer system, for example, or into a collection container.

Figure 2:
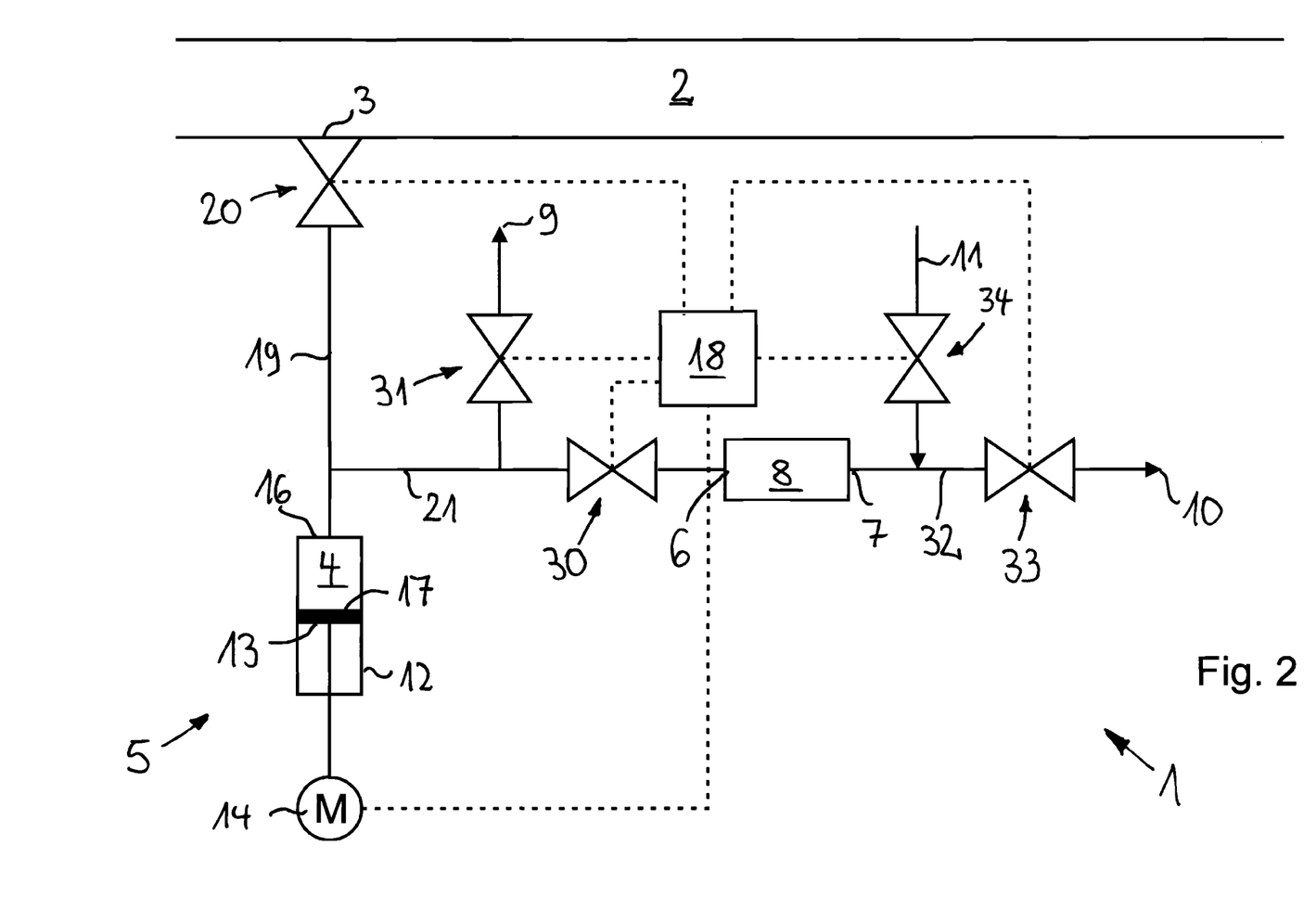

In the second exemplary embodiment shown in FIG. 2, the sampling device 1 shows a second and a third shutoff valve 30, 31 in place of the first three-way valve. The second shutoff valve 30 is disposed between the first line 19 and the particle filter 8 in the second line 21. The second line 21 has a connection location between the first line 19 and the second shutoff valve 30, which location is connected with the outlet opening 9 for waste by way of the third shutoff valve 31.

The outlet 7 of the particle filter 8 is connected with the discharging opening 10 for the beverage sample by way of a third line 32, in which a fourth shutoff valve 33 is disposed.

A second branching location, at which the third line 32 is connected with the feed line 11 for the backflushing medium by way of a fifth shutoff valve 34, is disposed between the outlet 7 of the particle filter 8 and the fourth shutoff valve 33.

The control device 18 stands in a control connection with the shutoff valves 20, 30, 33, 34 and the drive 14 of the pump 5, in such a manner that steps i) to vi) mentioned above are performed. For the remainder, the second exemplary embodiment essentially corresponds to the exemplary embodiment of FIG. 1.

Figure 3:
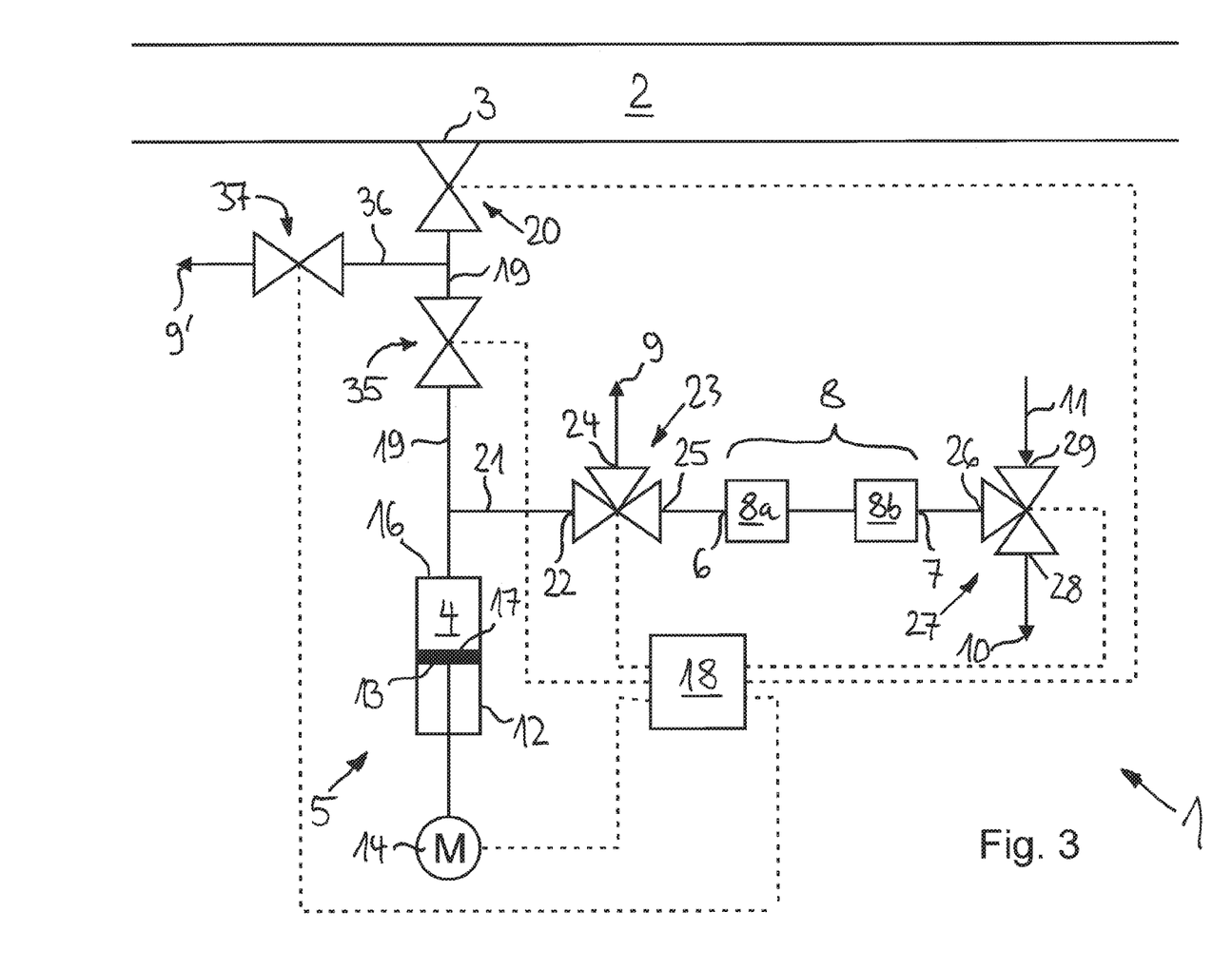

The third exemplary embodiment shown in FIG. 3 essentially corresponds to the first exemplary embodiment, but additionally has a sixth and a seventh shutoff valve 35, 37. The sixth shutoff valve 35 is disposed in the first line 19 between the first shutoff valve 20 and the first branching location, at which the second line 21 branches off from the first line 19. A third branching location is disposed between the first shutoff valve 20 and the sixth shutoff valve 35, at which the first line 19 is connected with a further outlet opening 9' for waste, by way of a fourth line 36, in which a seventh shutoff valve 37 is disposed. The first, sixth, and seventh shutoff valves 20, 35, 37 are configured in such a manner than when a cleaning fluid, disinfection fluid and/or flushing fluid is/are passed through the beverage line 2, the first and seventh shutoff valves 20, 37 are open, and the sixth shutoff valve 35 is closed. For filling the pump chamber 4 with the beverage sample, the first and sixth shutoff valves 20, 35 are open, and the seventh shutoff valve 37 is closed.

Figure 4:
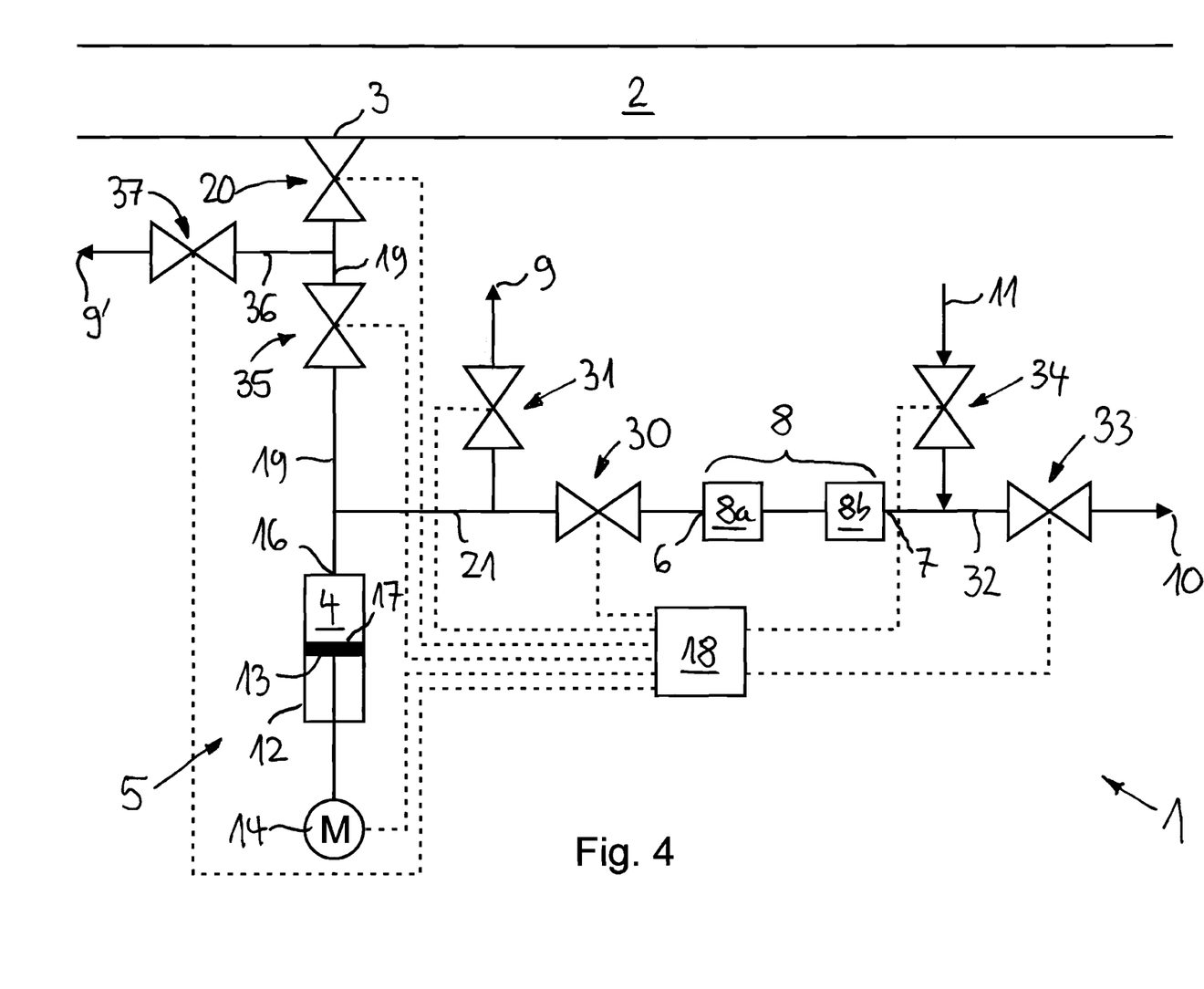

In the fourth exemplary embodiment shown in FIG. 4, the sampling device 1 has the second and third shutoff valves 30, 31 instead of the first three-way valve 23. The second shutoff valve 30 is disposed between the first branching location and the particle filter 8, in the second line 21.

The second line 21 has a connection location between the first line 19 and the second shutoff valve 30, which location is connected with the outlet opening 9 for waste by way of the third shutoff valve 31.

The outlet 7 of the particle filter 8 is connected with the discharging opening 10 for the beverage sample by way of a third line 32 in which is disposed the fourth shutoff valve 33. The second branching location, at which the third line 32 is connected with the feed line 11 for the backflushing medium by way of the fifth shutoff valve 34, is disposed between the outlet 7 of the particle filter 8 and the fourth shutoff valve 33.

In the fourth exemplary embodiment, the particle filter 8 has a pre-filter 8a and a micro-filter 8b, which is disposed behind the pre-filter 8a in the flow direction of the beverage sample. The micro-filter 8b has a lesser average pore diameter than the pre-filter 8a.

For the remainder, the fourth exemplary embodiment essentially corresponds to the exemplary embodiment of FIG. 3.

Figure 5:
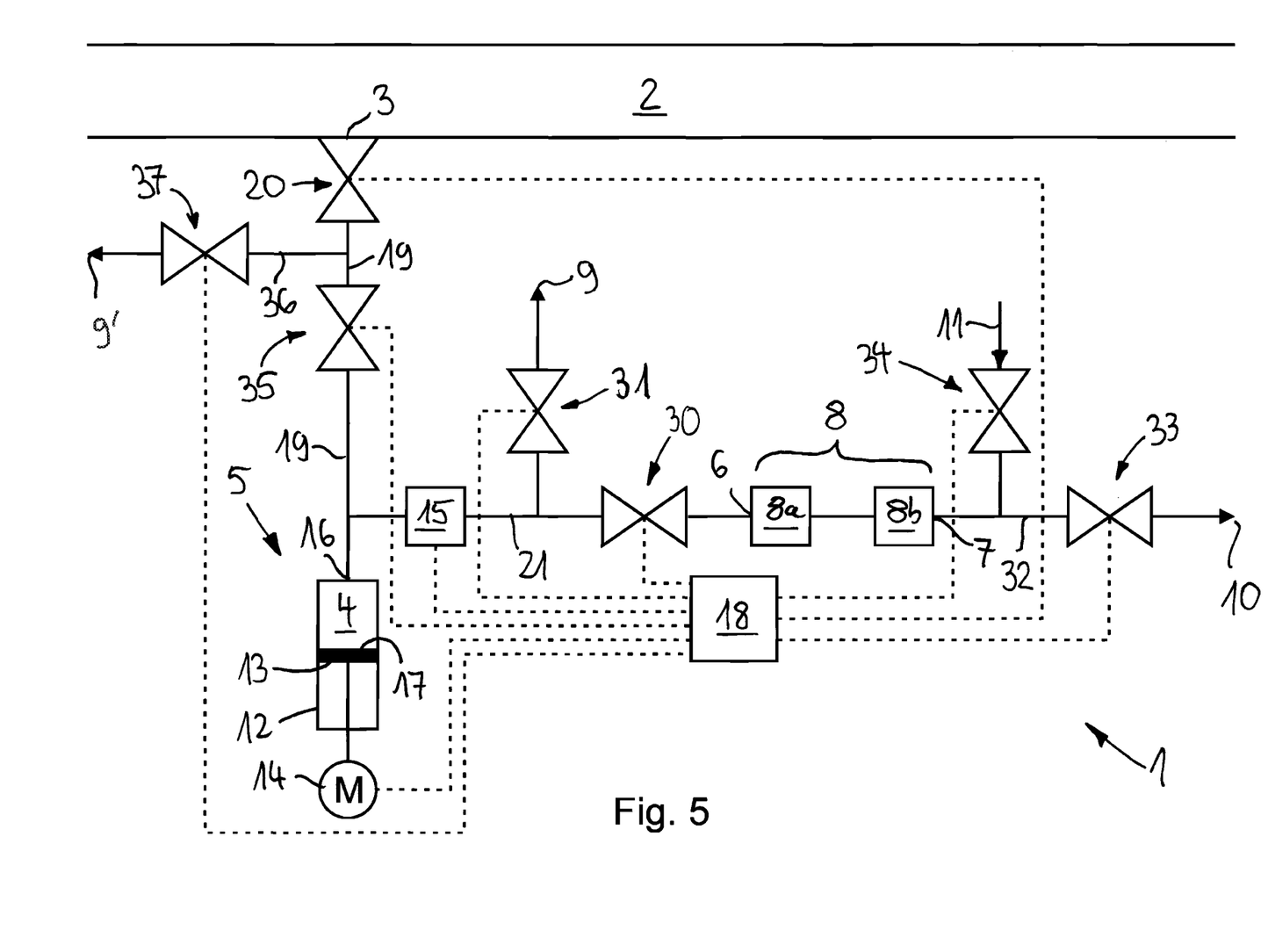

In the fifth exemplary embodiment shown in FIG. 5, a sensor 15 for detecting the beverage, connected with the control device 18, is disposed in the second line 21, between the first line 19 and the third shutoff valve, which sensor is configured as a pH sensor. The measurement signal of the sensor 15 is compared with a reference range in the control device 18, in which range the measurement signal lies when the sensor 15 is in contact with the beverage sample. When the sensor 15 is in contact with the gas that has exited from the beverage sample and/or with the cleaning fluid, disinfection fluid and/or flushing fluid, the measurement signal of the sensor 15 deviates from the reference range. In this case, the third shutoff valve 31 is locked in the closed position. In this way, gas, cleaning fluid, disinfection fluid and/or flushing fluid is/are prevented from entering into the particle filter 8. For the remainder, the fifth exemplary embodiment corresponds to the exemplary embodiment of FIG. 4.

Figure 6:
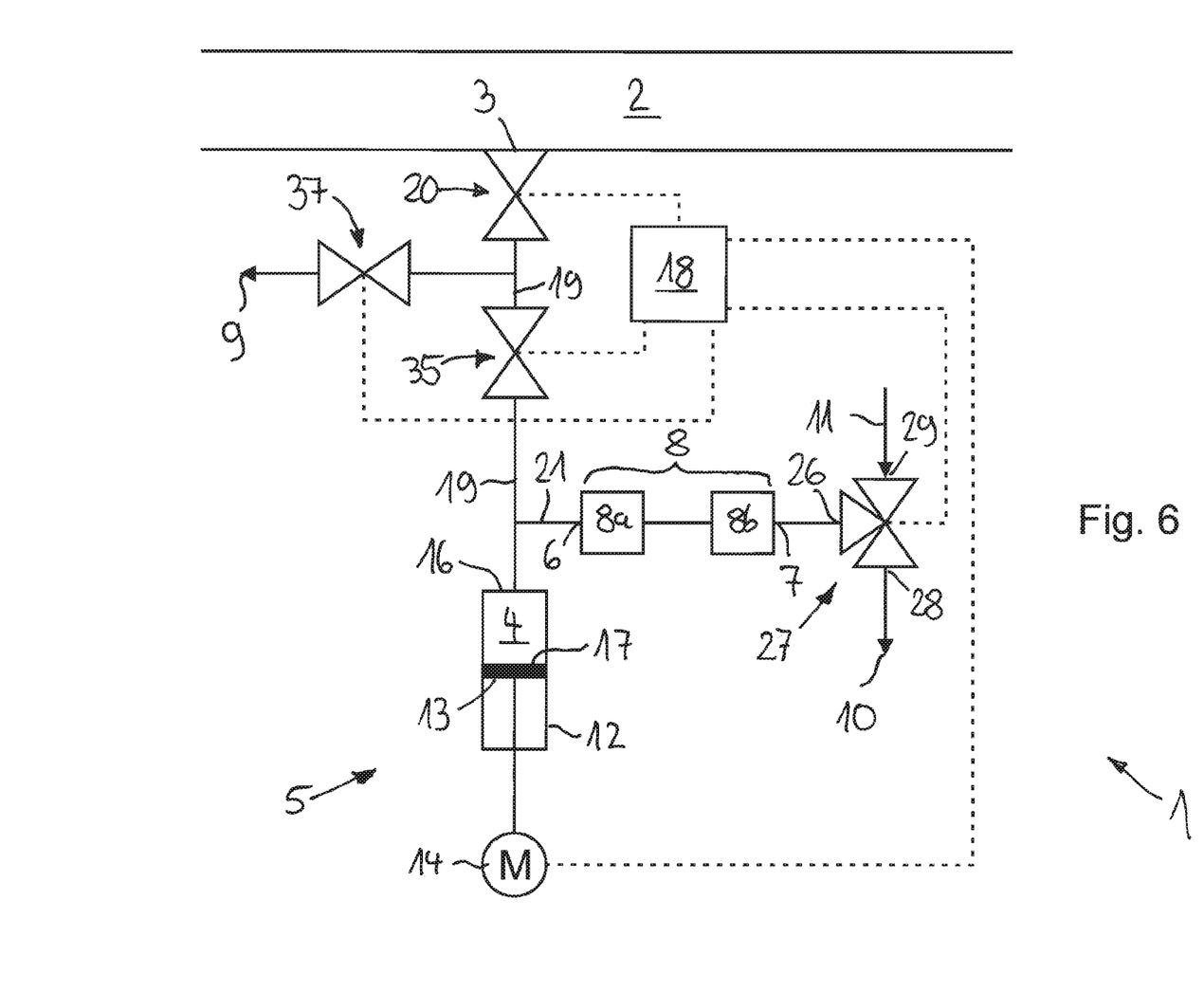

The line system of the sixth exemplary embodiment shown in FIG. 6 corresponds to the one in FIG. 3, but without the first three-way valve 23, i.e. the first line 19 is directly connected with the inlet 6 of the particle filter 8 in FIG. 6.

In the first valve configuration, the first and sixth shutoff valves 20, 35 are open to introduce the beverage sample into the pump chamber 4, and the seventh shutoff valve 37 is closed. Furthermore, the pump chamber 4 is separated from the discharging opening 10 for the beverage sample and the feed line 11 for the backflushing medium by means of the second three-way valve 27.

In the second valve configuration, the sixth shutoff valve 35 is closed for degassing the beverage sample situated in the pump chamber 4, and the pump chamber 4 continues to be separated from the discharging opening 10 and the feed line 11 by means of the second three-way valve 27.

In the third valve configuration, the first shutoff valve 20 is closed, and the sixth and seventh shutoff valves 35, 37 are open, so that the gas can be conducted away out of the pump chamber 4 to the outlet opening 9 for waste that is disposed behind the seventh shutoff valve 37. The pump chamber 4 continues to be separated from the discharging opening 10 and the feed line 11 by way of the second three-way valve 27.

In the fourth valve configuration, the first shutoff valve 20 is closed, and the pump chamber 4 is connected with the discharging opening 10 by way of the pre-filter 8a, the micro-filter 8b, and the second three-way valve 27.

In the fifth valve configuration, the feed line 11 for the backflushing medium is connected with the outlet 7 of the micro-filter 8b by way of the second three-way valve 27, and the inlet of the pre-filter 8a is connected with the outlet 9 for waste by way of the sixth and seventh shutoff valves 35, 37. The discharging opening 10 is separated from the feed line 11 and the outlet 7 of the micro-filter 8b by means of the second three-way valve 27. The first shutoff valve 20 is closed.

The invention claimed is:

1. A sampling device for taking beverage samples from a beverage line containing a carbonated beverage under pressure, wherein the sampling device has
   a connector for the beverage line,
   a pump having a drive, which pump has a pump chamber that is delimited by walls, which can be moved toward and away from one another, by means of the drive, for expanding and compressing the pump chamber,
   a discharging opening for the beverage sample,
   a line system having adjustable valves, which system is connected with the connector for the beverage line, the pump chamber, and the discharging opening, and
   a control device,
   wherein an outlet opening for waste is connected with the line system, and that the line system is configured in such a manner
   I) that in a first valve configuration, the pump chamber is connected with the connector for the beverage line, and separated from the outlet opening and the discharging opening,
   II) that in a second valve configuration, the pump chamber is separated from the connector for the beverage line, the outlet opening, and the discharging opening,
   III) that in a third valve configuration, the pump chamber is connected with the outlet opening, and separated from the connector for the beverage line and the discharging opening,
   IV) that in a fourth valve configuration, the pump chamber is connected with the discharging opening, and separated from the connector for the beverage line and the outlet opening,
   and that the control device is configured to control the pump and the valves, in such a manner
   i) that in the first valve configuration, a beverage sample, the volume of which is less than the maximal volume of the pump chamber, can be introduced from the connector for the beverage line into the pump chamber,
   ii) that afterward, the second valve configuration is set, and the pump chamber is expanded in such a manner that a partial vacuum occurs in the pump chamber, to remove gas from the beverage sample, wherein a first partial volume is the removed gas and is situated in an upper part of the pump chamber and a second partial volume is the beverage sample and is situated in a lower part of the pump chamber,
   iii) that afterward, the third valve configuration is set, and the pump chamber is compressed in such a manner that the first partial volume situated in the upper part of the pump chamber is displaced toward the outlet opening, and the second partial volume situated in the lower part of the pump chamber remains in the pump chamber, and
   iv) that afterward, the fourth valve configuration is set, and the pump chamber is compressed further so as to displace the beverage sample situated in it toward the discharging opening.

2. The sampling device according to claim 1, wherein the control device is configured in such a manner that steps ii) and iii) of claim 1 are repeated at least once before step iv) of claim 1 is carried out.

3. The sampling device according to claim 1, wherein the sampling device has a particle filter having an inlet and an outlet for the beverage sample, for filtering the beverage sample, the line system is connected with the inlet of the particle filter, the outlet of the particle filter, and a feed line for a backflushing medium, in the fourth valve configuration, the pump chamber is connected with the discharging opening by way of the particle filter, in the first, second, third, and fourth valve configuration, the pump chamber is separated from the feed line for the backflushing medium, in a fifth valve configuration, the feed line for the backflushing medium is connected with the outlet opening by way of the particle filter, and the control device is configured to control the valves, in such a manner that after step iv) of claim 1 for backflushing the particle filter, the fifth valve configuration is set.

4. The sampling device according to claim 1, wherein in the second and/or third valve configuration, the pump chamber is separated from the inlet of the particle filter.

5. The sampling device according to claim 4, wherein the particle filter has a pre-filter and a micro-filter set in series with it, and that the inlet of the particle filter is disposed on the pre-filter, and the outlet of the particle filter is disposed on the micro-filter.

6. The sampling device according to claim 4, wherein the connector for the beverage line is connected with the pump chamber by way of a first line, a first shutoff valve is disposed in the first line, and the pump chamber is connected with a first fluid connector of a first three-way valve, by way of a second line that opens into the pump chamber.

7. The sampling device according to claim 6, wherein at least one sensor connected with the control device, for detecting the beverage, is disposed in the line system between the connector for the beverage line and the inlet of the particle filter and/or between the pump chamber and the inlet of the particle filter, and the control device is configured in such a manner that the inlet of the particle filter is made inaccessible by means of the first three-way valve or the second shutoff valve if the sensor does not detect the beverage.

8. The sampling device according to claim 7, wherein the sensor has a conductivity sensor and/or a pH sensor.

9. The sampling device according to claim 4, wherein the connector for the beverage line is connected with the pump chamber by way of a first line, a first shutoff valve is disposed in the first line, and the pump chamber is connected with the inlet of the particle filter by way of a second line, which opens into the pump chamber or is connected with the first line at a first branching location disposed between the chamber.

10. The sampling device according to claim 4, wherein the connector for the beverage line is connected with the first line at a first branching location disposed between the chamber and the first shutoff valve, a second fluid connector of the first three-way valve is connected with the outlet opening, and a third fluid connector of the first three-way valve is connected with the inlet of the particle filter.

11. The sampling device according to claim 10, wherein at least one sensor connected with the control device, for detecting the beverage, is disposed in the line system between the connector for the beverage line and the inlet of the particle filter and/or between the pump chamber and the inlet of the particle filter, and the control device is configured in such a manner that the inlet of the particle filter is closed by means of the first three-way valve or the second shutoff valve if the sensor does not detect the beverage.

12. The sampling device according to claim 11, wherein the sensor has a conductivity sensor and/or a pH sensor.

13. The sampling device according to claim 4, wherein the connector for the beverage line is connected with the first line at a first branching location disposed between the chamber and the first shutoff valve, a second shutoff valve is disposed in the second line, and a connection location is provided on the pump chamber and/or on the first line, between the pump chamber and the first shutoff valve, and/or on the second line, between the pump chamber and the second shutoff valve, which location is connected with the outlet opening for waste by way of a third shutoff valve.

14. The sampling device according to claim 4, wherein the outlet of the particle filter is connected with a first fluid connector of a second three-way valve, a second fluid connector of the second three-way valve is connected with the discharging opening for the beverage sample, and a third fluid connector of the second three-way valve is connected with the feed line for the backflushing medium.

15. The sampling device according to claim 4, wherein the outlet of the particle filter is connected with the discharging opening for the beverage sample by way of a third line in which a fourth shutoff valve is disposed, and a second branching location is disposed between the outlet of the particle filter and the fourth shutoff valve, at which location the third line is connected with the feed line for the backflushing medium by way of a fifth shutoff valve.

16. The sampling device according to claim 4, wherein the connector for the beverage line is connected with the pump chamber by way of a first line, a first shutoff valve and a sixth shutoff valve are switched in series in the first line, that the pump chamber or a first branching location provided between the sixth shutoff valve and the pump chamber in the first line is connected with the inlet of the particle filter by way of a second line, and a third branching location is disposed between the first shutoff valve and the sixth shutoff valve, at which location the first line is connected with the outlet opening or a further outlet opening for waste by way of a fourth line, in which a seventh shutoff valve is disposed.

* * * * *